(12) United States Patent
Black

(10) Patent No.: US 7,722,278 B2
(45) Date of Patent: May 25, 2010

(54) TWIN DUCKBILL VALVE ASSEMBLY

(75) Inventor: Craig Black, Bellevue, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 583 days.

(21) Appl. No.: 10/581,217

(22) PCT Filed: Dec. 9, 2004

(86) PCT No.: PCT/IB2004/052738

§ 371 (c)(1),
(2), (4) Date: Jan. 9, 2007

(87) PCT Pub. No.: WO2005/058186

PCT Pub. Date: Jun. 30, 2005

(65) Prior Publication Data

US 2007/0113903 A1    May 24, 2007

Related U.S. Application Data

(60) Provisional application No. 60/528,636, filed on Dec. 11, 2003.

(51) Int. Cl.
    *A47L 13/22*    (2006.01)

(52) U.S. Cl. ...................... 401/287; 401/286
(58) Field of Classification Search ............... 401/270, 401/282, 286, 287, 291; 137/512.15, 847
    See application file for complete search history.

(56) References Cited

U.S. PATENT DOCUMENTS

| | | | | |
|---|---|---|---|---|
| 1,988,557 | A | * | 1/1935 | Jecker ........................ 401/271 |
| 5,746,532 | A | * | 5/1998 | Megill et al. ................ 401/175 |
| 5,931,596 | A | * | 8/1999 | Javier ........................ 401/268 |
| 6,027,273 | A | | 2/2000 | Li |
| 6,648,641 | B1 | | 11/2003 | Viltro et al. |
| 6,834,677 | B2 | * | 12/2004 | Barinaga et al. ............. 137/846 |
| 2002/0044817 | A1 | | 4/2002 | Hall et al. |
| 2002/0090252 | A1 | | 7/2002 | Hall et al. |
| 2002/0108193 | A1 | | 8/2002 | Gruber |
| 2003/0201023 | A1 | | 10/2003 | Barinaga et al. |

* cited by examiner

*Primary Examiner*—David J Walczak

(57) ABSTRACT

The duckbill valve assembly includes at least two duckbill valve members and a flexible, flat flange member which joins the two duckbill valve members together. The flange connects the duckbill valve members together at their respective bases, thereby maintaining the two duckbill valve members in a particular orientation and arrangement relative to each other.

10 Claims, 3 Drawing Sheets

TWIN DUCKBILL VALVE ASSEMBLY

CROSS REFERENCE TO RELATED APPLICATION

This application claims the benefit of U.S. provisional application Ser. No. 60/528,636 filed Dec. 11, 2003, which is incorporated herein whole by reference.

This invention relates generally to the field of duckbill valves, and more specifically concerns a new duckbill valve arrangement.

Duckbill valves are in general well known. A duckbill valve includes a slit at a front (upper) end thereof which under positive differential pressure opens to permit exit of fluid therethrough. Otherwise, the slit is closed and resistant to backflow under negative pressure. Various shapes and sizes of duckbill valves are used for particular applications. One example is the use of a duckbill valve in fluid-dispensing toothbrushes.

However, the currently available duckbill valves used in toothbrushes have been known to fall out of the toothbrush bristle plate, or can be easily pulled out from the bristle plate in which they are mounted. Further, there is typically no easy, reliable way to properly orient the duckbill valve in the bristle plates using automated manufacturing equipment. Hence, the duckbill valve may end up with the slit at various orientations in the bristle plate.

In addition, conventional duckbill valves can become clogged, or the exiting fluid may not cover the desired area because of limitations in existing duckbill valve configurations. Further, particularly for toothbrushes, there may be a need to deliver more than one fluid, which results in fluid path complexity to the duckbill valve.

It would be desirable to have a duckbill valve which overcomes one or more of the disadvantages discussed above.

Accordingly, the present invention is a duckbill valve assembly, comprising:

At least two duckbill valve members; and a flange member which extends between and joins the duckbill valve members in a particular orientation.

Figure 2:
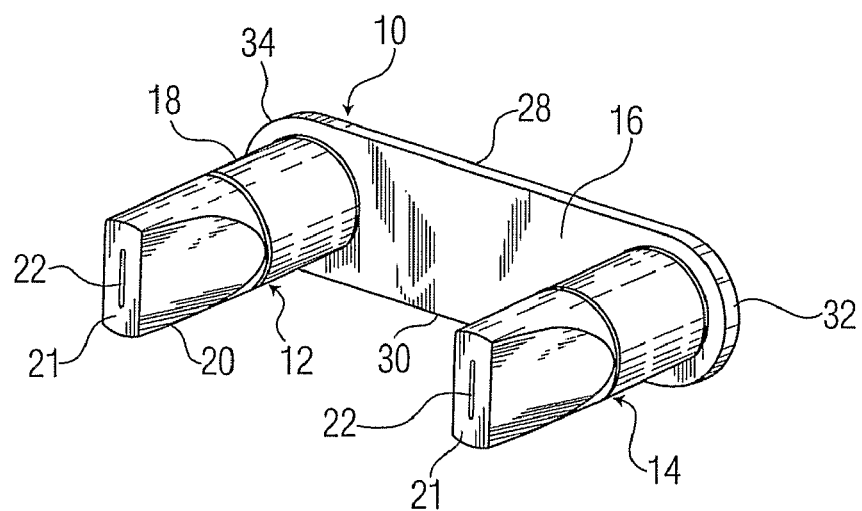
FIG. 2 is a perspective view of the duckbill valve shown in FIG. 1.

Referring now to FIG. 2, the twin duckbill valve assembly of the present invention, shown generally at 10, includes two individual duckbill valve members 12 and 14 joined by a flange 16 at the respective bases thereof. Duckbill valve members 12 and 14 are similar to conventional duckbill valves in that they have a circular lower portion 18 and a tapered upper portion 20 with a rectangular upper surface 21. Each duckbill valve member 12 and 14 is hollow, with an open base (lower end) to receive fluid and a slit 22 in upper surface 21 which extends for most of the length of upper surface 21, through which fluid exits the valve. The duckbill valve members 12 and 14 are made from a flexible material, such as rubber.

Under positive differential pressure, slit 22 opens to allow the free flow of fluid through the valve. Under negative pressure, backflow through the valve is prevented because the slit 22 remains firmly closed. Again, the basic structure of a duckbill valve is well known; a wide variety of duckbill valve sizes and configurations are available from various manufactures for different applications.

In applicant's invention, flange 16 joins the base of the two duckbill valve members, thereby creating a unitary article and maintaining the separate valve members in a fixed spatial relationship.

In the embodiment shown, flange 16 is also made of flexible material and is approximately 0.5 mm thick. While flange 16 can have various configurations, the configuration shown in FIG. 2, which includes two straight parallel longitudinal sides 28 and 30, with curved end portions 32 and 34 joining the longitudinal sides and extending slightly beyond the edge of the duckbill valve members, is preferred for ease of manufacturing. In the embodiment shown, flange 16 is 13.8 mm long, approximately 4.2 mm wide, with the centerlines of the two duckbill members being separated by 10.5 mm. These dimensions can be varied for different applications.

Figure 1:
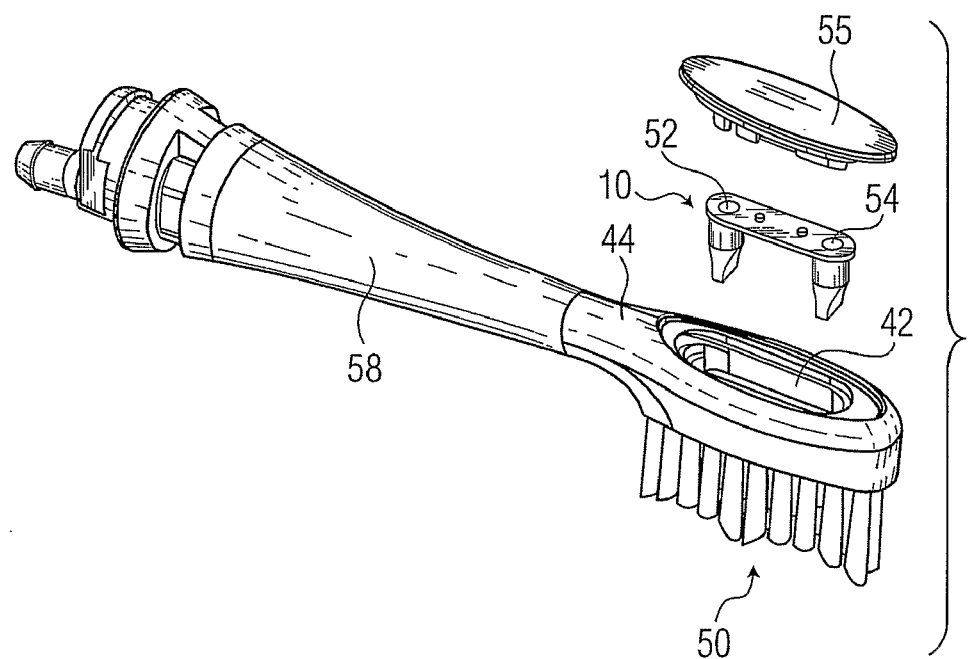
FIG. 1 is an exploded view showing the duckbill valve of the present invention in a stem/brushhead portion of a toothbrush.
Figure 3:
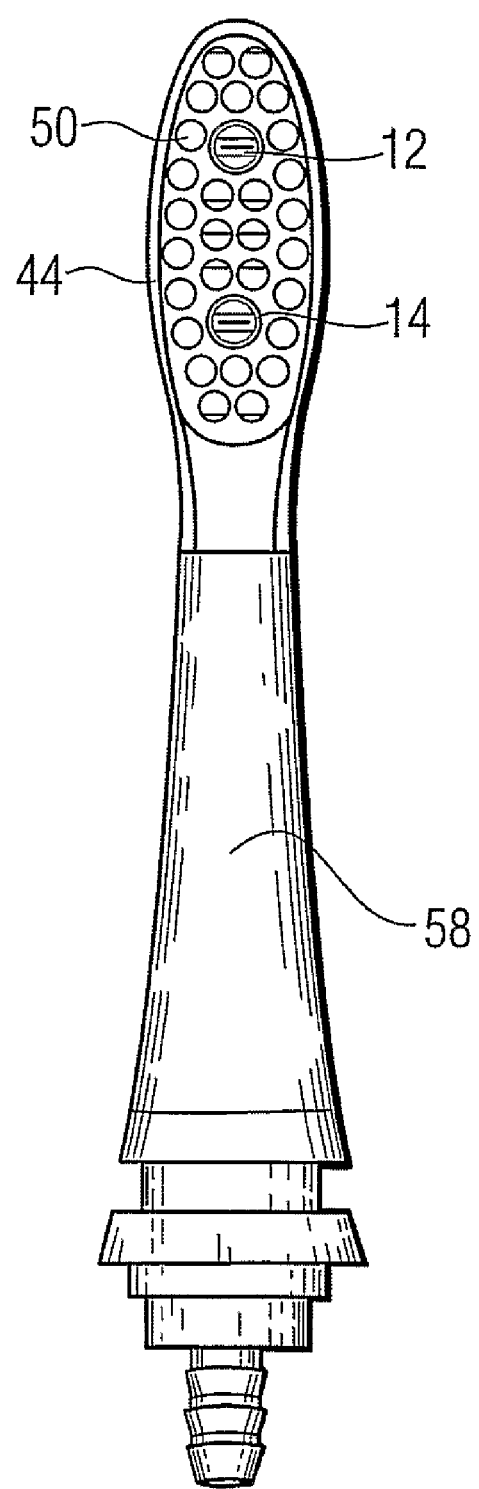
FIG. 3 is a front view of a toothbrush stem/brushhead with the duckbill valve of FIGS. 1 and 2.
Figure 4:
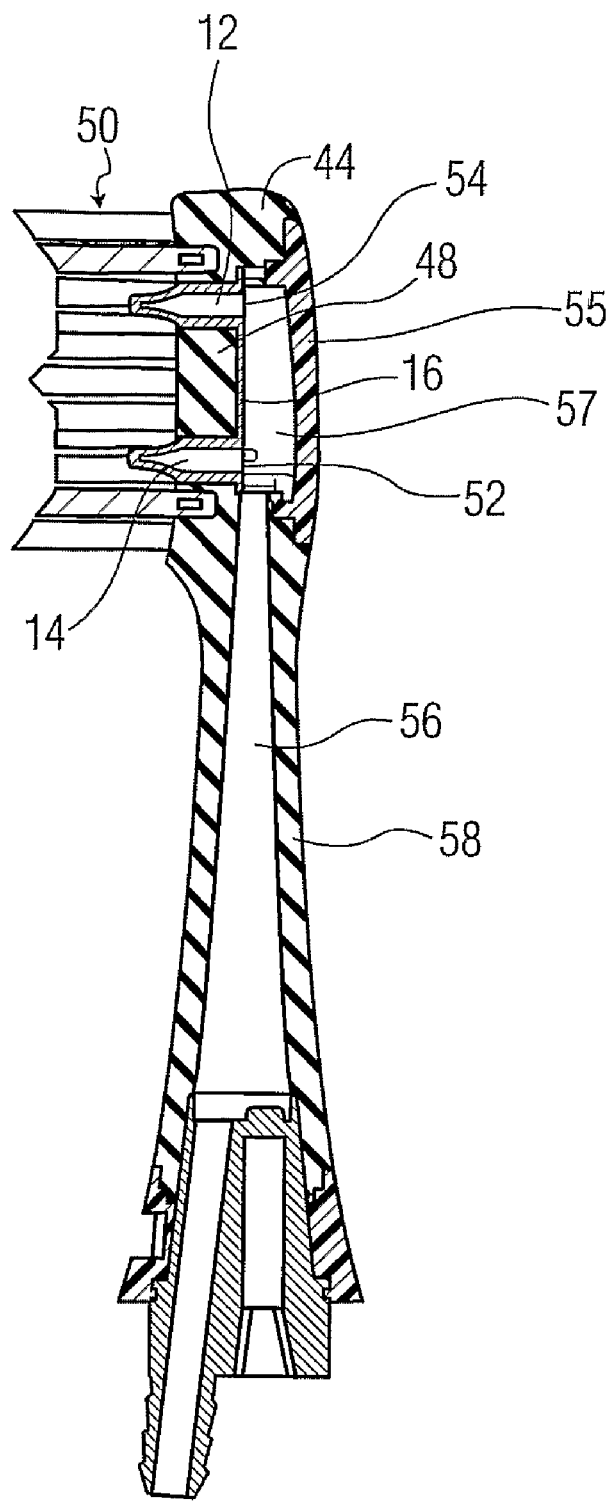
FIG. 4 is a cross-sectional view of a toothbrush brushhead with the duckbill valve of FIGS. 1 and 2.

FIG. 1 shows an exploded view of the twin duckbill valve assembly 10 in a toothbrush application. FIGS. 3 and 4 show views of the assembled combination. Duckbill valve assembly 10 is inserted into a cavity 42 in bristle plate 44, with the two individual duckbill valve members 12 and 14 extending through spaced openings in a remaining thickness portion 48 of the bristle plate, such that they extend into the field of bristles 50 mounted on the bristle plate 44. A holding member 55 is then positioned over the duckbill valve assembly 10 in cavity 42, holding the assembly in place therein against the remaining thickness portion 48 of the bristle plate. The inserted holding member is configured to define cavities 57 or channels in the bristle plate which receive fluid from a reservoir through stem portion 58. The open bases of the duckbill members are in fluid communication with the cavity in the bristle plate through openings 52 and 54 in flange 16. This arrangement allows fluid under positive pressure to flow into the individual duckbill valve members 12 and 14 and out through the slitted upper ends thereof into bristle field 50.

While the arrangement shown includes two individual duckbill valve members which are oriented such that their slits 22-22 are parallel to each other laterally across flange 16, the two duckbill valve members could be oriented so that the slits are in a single line along the toothbrush (in a single vertical plane).

Furthermore, it should be understood that there may be more than two duckbill valve members in a particular assembly. Still further, the individual duckbill valve members, respectively, could have different sizes and/or shapes, different from each other, to accommodate two different liquids. If the two duckbill valve members are connected to the same fluid path, however, it is advantageous for the two duckbill valve members to be of the same size, shape and orientation. Still further, in a toothbrush application, it is advantageous for the duckbill valve members to be separated by a distance, to accommodate bristles in the bristle field therebetween, such as shown particularly in FIG. 1.

There are several advantages to the multiple duckbill valve assembly of the present invention. First, it permits an easy automatic assembly with proper duckbill orientation, as the duckbill valve assembly can only fit into the bristle plate in one orientation. Still further, it is very difficult to pull the duckbill out from the bristle plate, since the flange 16 abuts the inner surface of the remaining thickness portion 48 of the bristle plate. Also, as indicated above, the present duckbill assembly structure can accommodate two separate fluid paths through the toothbrush stem for two different fluids. Hence, the multiple duckbill valve assembly of the present invention overcomes disadvantages of a single duckbill assembly, but also has additional advantages thereover.

Although a preferred embodiment of the invention has been disclosed for purposes of illustration it should be understood that various changes, modifications and substitutions may be incorporated in the embodiment without departed from the spirit of the invention which is defined by the claims as follows:

The invention claimed is:

1. A toothbrush brushhead assembly, comprising:
   a toothbrush stem;
   a bristle plate including a cavity;
   a duckbill valve assembly which includes at least two duckbill valve members; and
   a flexible flange member extending between and joining the duckbill valve members, such that the duckbill valves are flexibly movable relative to each other in a particular orientation in a unitary assembly which is insertable into and removable as a unit from the cavity.

2. The toothbrush of claim 1, wherein the flange member joins the two duckbill valve members at their respective bases, and wherein the flange member is substantially flat.

3. The toothbrush of claim 1, wherein the duckbill valve members have slit openings through which fluid moves and are spaced apart from each other, but arranged so that their respective slit openings are parallel.

4. The toothbrush of claim 1, wherein the duckbill valve members have slit openings through which fluid moves and are oriented such that their respective slit openings are in a single line.

5. The toothbrush of claim 1, wherein the duckbill valve members are substantially identical.

6. The assembly of claim 1, wherein the two duckbill valve members are sufficiently separated to permit a plurality of bristles to be mounted therebetween to the bristle plate.

7. The toothbrush of claim 1, wherein the duckbill valve assembly includes just two duckbill valve members.

8. The toothbrush of claim 1, wherein the duckbill valve assembly includes more than two duckbill valve members.

9. The toothbrush of claim 1, wherein the duckbill valve members are different in size and otherwise arranged to accommodate different fluids to flow therethrough.

10. The toothbrush of claim 1, wherein a holding member is disposed over the duckbill valve assembly in the cavity, holding the duckbill valve assembly against the bristle plate.

\* \* \* \* \*